(12) United States Patent
Furukawa

(10) Patent No.: US 9,211,068 B2
(45) Date of Patent: Dec. 15, 2015

(54) OBJECT INFORMATION ACQUIRING APPARATUS AND OBJECT INFORMATION ACQUIRING METHOD

(71) Applicant: CANON KABUSHIKI KAISHA, Tokyo (JP)

(72) Inventor: Yukio Furukawa, Sagamihara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 101 days.

(21) Appl. No.: 13/900,906

(22) Filed: May 23, 2013

(65) Prior Publication Data

US 2013/0331680 A1    Dec. 12, 2013

(30) Foreign Application Priority Data

Jun. 6, 2012    (JP) .................................. 2012-128980

(51) Int. Cl.
*A61B 5/00*    (2006.01)

(52) U.S. Cl.
CPC ........... *A61B 5/0095* (2013.01); *A61B 2576/00* (2013.01)

(58) Field of Classification Search
CPC . A61B 5/0093; A61B 5/0095; A61B 2576/00
USPC ................. 600/407, 443, 437, 473, 476–478; 73/602, 632, 655
See application file for complete search history.

(56) References Cited

U.S. PATENT DOCUMENTS

| 6,106,469 A | 8/2000 | Suzuki et al. | |
|---|---|---|---|
| 2011/0232385 A1* | 9/2011 | Nanaumi | 73/602 |
| 2011/0245652 A1 | 10/2011 | Oishi | |
| 2013/0061678 A1 | 3/2013 | Yamamoto et al. | 73/602 |
| 2013/0112001 A1 | 5/2013 | Furukawa | 73/655 |
| 2013/0231549 A1 | 9/2013 | Yamamoto et al. | |

FOREIGN PATENT DOCUMENTS

| JP | 2000-107177 | 4/2000 |
|---|---|---|
| JP | 2009-082450 | 4/2009 |

OTHER PUBLICATIONS

U.S. Appl. No. 14/014,752, filed Aug. 30, 2013.

* cited by examiner

*Primary Examiner* — Michael Rozanski
(74) *Attorney, Agent, or Firm* — Fitzpatrick, Cella, Harper & Scinto

(57) ABSTRACT

Disclosed is an object information acquiring apparatus including: a receiver that includes a plurality of elements and converts an acoustic wave generated from an object irradiated with light into a received signal, and outputs the received signal in a time series; a normalizer that generates a normalized signal by normalizing the intensity of the received signal; and a processor that generates, from the normalized signal, first image data that indicates the distribution of property information inside the object.

18 Claims, 11 Drawing Sheets

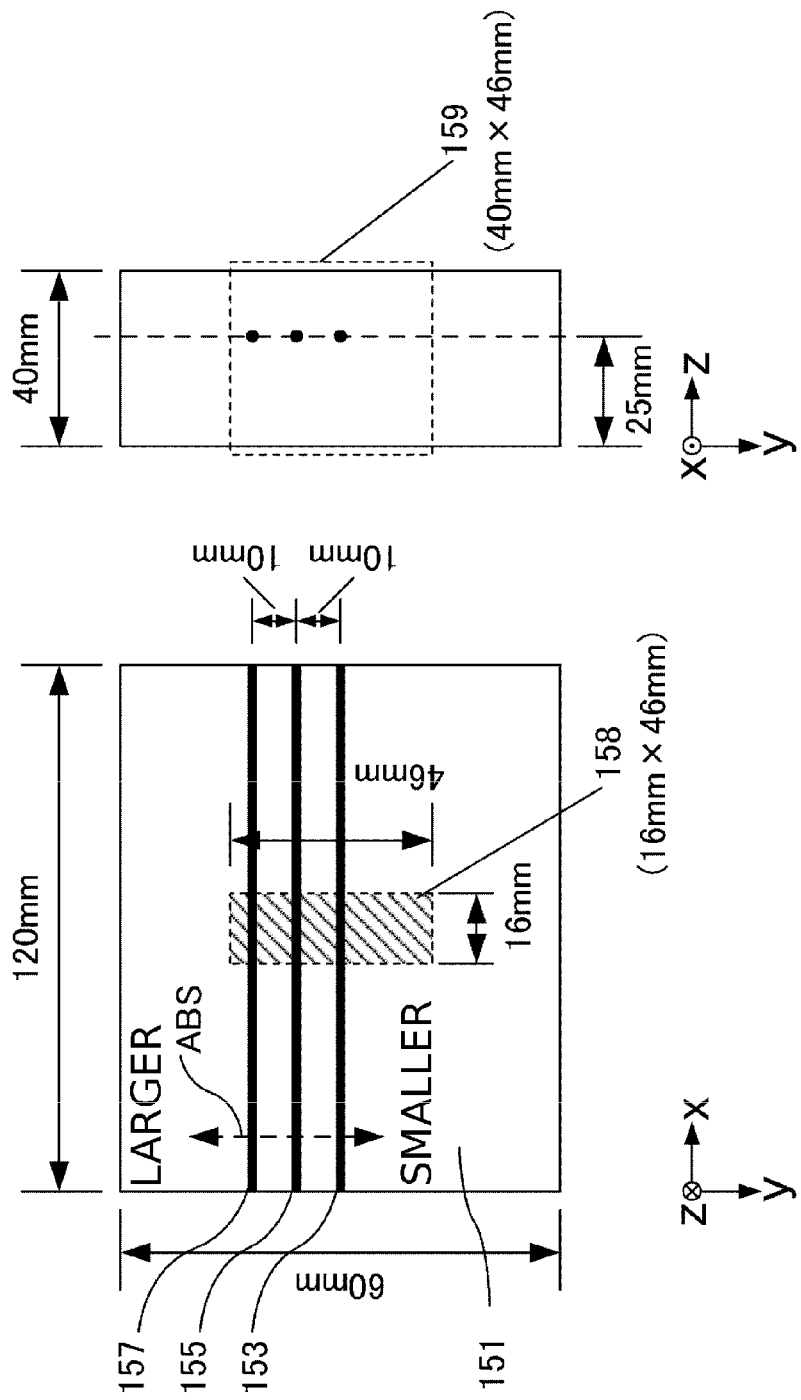

OBJECT INFORMATION ACQUIRING APPARATUS AND OBJECT INFORMATION ACQUIRING METHOD

BACKGROUND OF THE INVENTION

1. Field of the Invention

The present invention relates to an object information acquiring apparatus and an object information acquiring method.

2. Description of the Related Art

Vigorous research on optical imaging apparatuses that irradiate light from a light source such as a laser onto a biological object, and images the information inside the biological object acquired based on the entered light is in progress in the medical field. An example of an optical image technique is photoacoustic tomography (PAT). In PAT, pulsed light generated from a light source is irradiated onto a biological object, and an acoustic wave generated from biological tissue, which absorbed energy of the pulsed light that propagated and diffused inside the biological object, is detected. This phenomenon of generating the photoacoustic wave is called "photoacoustic effect", and the acoustic wave generated by the photoacoustic effect is called "photoacoustic wave".

In many cases, a test segment, such as a tumor, has a higher absorptivity of optical energy than peripheral tissue, and therefore instantaneously expands by absorbing more light than the peripheral tissue. The photoacoustic wave generated during this expansion is detected by an acoustic wave detector, and a received signal is acquired. By mathematically analyzing this received signal, the distribution of sound pressure of the photoacoustic wave generated by the photoacoustic effect inside the object can be imaged (hereafter called "photoacoustic image").

Based on the photoacoustic image acquired like this, the optical property distribution in the biological object, especially the absorption coefficient distribution, can be acquired. This information can be used for the quantitative measurement of a specific substance in the object, such as glucose and hemoglobin contained in blood. In recent years, vigorous research on photoacoustic imaging apparatuses aimed at imaging blood vessels of a small animal using PAT or applying PAT to the diagnosis of breast cancer or the like is ongoing.

An apparatus for acquiring a photoacoustic image may include a holding plate for holding an object. This is to prevent the object from moving and the position during measurement from changing, and/or making the object thinner by the pressure of the holding plate so as to image the deep portion of the object.

If light is irradiated onto the object held by the holding plate, a photoacoustic wave is generated by the photoacoustic effect not only inside the object, but also in the interface of the holding plate. The photoacoustic wave from the interface of the holding plate is called "interfacial photoacoustic wave". If this interfacial photoacoustic wave is detected by the acoustic wave detector, noise called "artifact" may be generated.

In concrete terms, if a photoacoustic image is acquired using a received signal including an interfacial photoacoustic wave, an image of a tumor or the like may be hidden by an artifact due to the interfacial photoacoustic wave. The interfacial photoacoustic wave may also be detected by the acoustic wave detector after being multi-reflected inside the holding plate. If a photoacoustic image is acquired using a received signal including a multi-reflected interfacial photoacoustic wave, an image of a tumor or the like may be hidden by an artifact, just like the case of the interfacial photoacoustic wave.

A problem similar to the problem of the interfacial photoacoustic wave in a photoacoustic imaging apparatus also occurs in an ultrasonic diagnostic apparatus. In concrete terms, a transmitted ultrasound repeats multi-reflection inside an interposing object between the acoustic wave detector and the object, such as an acoustic window or an object pressing plate, and appears in an image as a multi-echo artifact.

Japanese Patent Application Laid-Open No. 2000-107177 discloses a method for removing multi-echo generated by an acoustic window constituting an ultrasonic diagnostic apparatus. In Japanese Patent Application Laid-Open No. 2000-107177, multi-echo is removed by subtracting multi-echo extracted by averaging a plurality of received signals from the received signals.

Japanese Patent Application Laid-Open No. 2009-082450 discloses a method for removing a multi-reflected image generated by a plate for pressing an object, which constitutes a medical imaging apparatus to display an ultrasonic diagnostic image. In Japanese Patent Application Laid-Open No. 2009-082450, image data to represent a plurality of ultrasonic images is generated, and a multi-reflected image is extracted from the generated image data. The multi-reflected image is removed by subtracting the extracted multi-reflected image from the image of the object.

Patent Literature 1: Japanese Patent Application Laid-Open No. 2000-107177

Patent Literature 2: Japanese Patent Application Laid-Open No. 2009-082450

SUMMARY OF THE INVENTION

In a photoacoustic image apparatus, a photoacoustic wave is normally detected at a plurality of different positions. In other words, a photoacoustic wave is simultaneously detected at a plurality of different positions using an acoustic detector array having a plurality of elements. Thereby measurement time can be decreased. Light is irradiated so that an object area on the front face of the acoustic detector array is illuminated. The light irradiated in this case normally has spatial intensity distribution.

The amplitude of a photoacoustic wave generated by a photoacoustic effect is in proportion to the intensity distribution of the light. Therefore the above mentioned interfacial photoacoustic wave has a spatial sound pressure distribution that is in proportion to the spatial intensity distribution of the light, which is irradiated onto the interface of the object. In the same manner, the multi-reflected interfacial photoacoustic wave also has spatial sound pressure distribution.

The acoustic wave detector array detects an interfacial photoacoustic wave having a spatial sound pressure distribution. Therefore the amplitude of the interfacial photoacoustic wave to be detected is different depending on each element of the acoustic wave detector array. Hence if the method according to Japanese Patent Application Laid-Open No. 2000-107177 is used, which averages a plurality of received signals of which amplitudes are different from one another are averaged, therefore the amplitude of the multi-echo to be extracted does not always match the amplitude of the multi-echo in the received signal. This means that it is difficult to sufficiently subtract a multi-echo.

The method of Japanese Patent Application Laid-Open No. 2009-082450 requires a plurality of times of measurement since the image data representing a plurality of ultrasonic images are required. This means that the measurement time increases.

With the foregoing in view, it is an object of the present invention to acquire a high contrast photoacoustic image, where artifacts are decreased.

The present invention provides an object information acquiring apparatus, comprising:

a receiver having a plurality of elements configured to convert an acoustic wave generated from an object irradiated with light into a received signal, and output the received signal in a time series;

a normalizer configured to generate a normalized signal by normalizing an intensity of the received signal; and a processor configured to generate, from the normalized signal, first image data that indicates a distribution of property information inside the object.

The present invention also provides an object information acquiring method, comprising the steps of:

a receiver converting an acoustic wave generated from an object irradiated with light into a received signal, and outputting the received signal in a time series;

a normalizer generating a normalized signal by normalizing an intensity of the received signal; and a processor generating, from the normalized signal, first image data that indicates a distribution of property information inside the object.

According to the present invention, a high contrast photoacoustic image, where artifacts are decreased, can be acquired.

Further features of the present invention will become apparent from the following description of exemplary embodiments with reference to the attached drawings.

BRIEF DESCRIPTION OF THE DRAWINGS

FIG. 2A and FIG. 2B are diagrams depicting an object according to Example 1;

DESCRIPTION OF THE EMBODIMENTS

Figure 1:
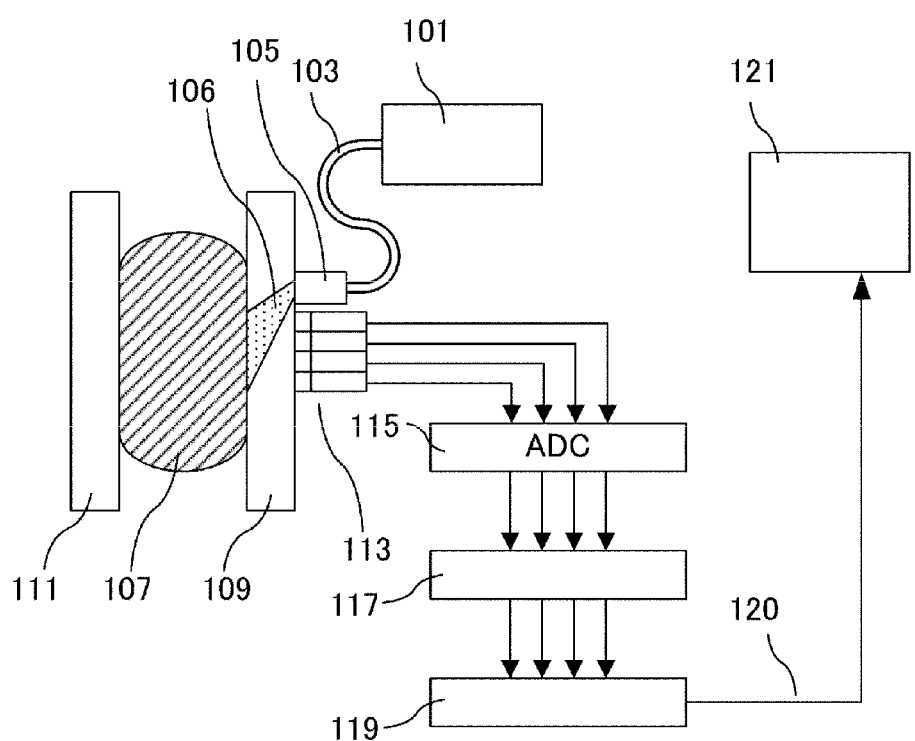
FIG. 1 is a conceptual diagram depicting a configuration of an apparatus of Example 1.

Preferred embodiments of the present invention will now be described with reference to the drawings. The sizes, materials, and shapes of components described hereinbelow, and the relative positions of these elements can be appropriately changed depending on the configuration and various conditions of the apparatus to which the invention is applied, and the scope of the invention is not limited to the following description.

A photoacoustic measurement apparatus of the present invention includes an apparatus utilizing a photoacoustic effect, which receives an acoustic wave generated in an object by irradiating light (electromagnetic wave) onto the object, and acquires property information inside the object as image data.

The property information of the object includes a generation source distribution of an acoustic wave generated by irradiating the light, an initial sound pressure distribution inside the object, an optical energy absorption density distribution and an absorption coefficient distribution derived from the initial sound pressure distribution, and a density distribution of a substance constituting the tissue. The density distribution of a substance is, for example, an oxygen saturation degree distribution, oxyhemoglobin distribution, and deoxyhemoglobin distribution. Such property information is also called "object information", hence the photoacoustic measurement apparatus of the present invention can also be called "object information acquiring apparatus".

The acoustic wave in the present invention is typically an ultrasonic wave, and includes an elastic wave that is also called "sound wave", an ultrasonic wave and an acoustic wave. An acoustic wave generated by the photoacoustic effect is called "photoacoustic wave". An acoustic wave detector (e.g. probe) receives an acoustic wave generated or reflected inside the object.

<Configuration of Photoacoustic Measurement Apparatus>

Preferred embodiments of each component constituting the photoacoustic measurement apparatus according to the present invention will now be described.

(Pulsed Light Source)

If an object is a biological object, a light source irradiates light having a wavelength that is absorbed by a specific component out of components constituting the biological object. The light source may be integrated with the photoacoustic measurement apparatus or may be a separate unit. In order to generate the photoacoustic wave efficiently, it is preferable that the pulse width is about 10 nsecs to 50 nsecs. A laser which can provide large output is desirable as the light source, but a light emitting diode, a flash lamp or the like can also be used. For the laser, various lasers can be used, including a solid-state laser, a gas laser, a dye laser and a semiconductor laser. A light source controller controls the timing, waveform and intensity of irradiation. The light source controller may be integrated with the light source. It is desirable that the light to be irradiated has a wavelength that allows the light to propagate into the inside of the object. In concrete terms, the desired wavelength is 500 nm or more and 1200 nm or less if the object is a biological object.

(Optical Transmission Unit)

The light emitted from the pulsed light source reaches an optical irradiation unit by an optical transmission unit. The optical transmission unit has an optical waveguide structure, such as an optical fiber or a bundle fiber in which a plurality of optical fibers are bundled. The optical transmission unit may be a type of propagating light in a space using such an optical element as a mirror or a lens.

(Optical Irradiation Unit)

The light guided by the optical transmission unit is irradiated onto the object, such as a biological object, by the optical irradiation unit. It is preferable that the intensity, light distribution and position of the irradiation light are adjusted by such an optical element as a mirror, a lens or a prism. A position where the optical irradiation unit is installed is a same side as an acoustic wave detector with respect to the object, an opposite side of the acoustic wave detector with respect to the object, or both sides of the acoustic wave detector.

(Acoustic Detector)

The acoustic detector receives a photoacoustic wave which is generated by the irradiated pulsed light on the surface of and inside the object, and converts the photoacoustic wave into an electric signal, which is an analog signal. This electric signal is called "received signal". The photoacoustic wave detector generates and outputs received signals in a time series. The photoacoustic wave detector corresponds to the receiver of the present invention.

If a signal processor performs digital conversion processing on the analog received signal, as pre-processing for the later mentioned normalization processing and imaging processing, the signal after the conversion can also be called "received signal". Even if the received signal is a discrete digital signal like this, it can be said that the signal is generated in a time series if the signal is continuously outputted for a specific period.

For the acoustic wave detector, any type can be used if an acoustic wave can be received, such as a type using the piezoelectric phenomena, a type using the resonance of light, and a type using the change of electrostatic capacity. Typically an acoustic wave detector in which a plurality of receiver elements are arrayed one dimensionally or two dimensionally is preferable. By using such elements in a multi-dimensional array, an acoustic wave can be received simultaneously at a plurality of positions, and measurement time can be decreased. If there is only one receiver element, the acoustic wave may be received at a plurality of positions by scanning the receiver element.

(Signal Processor)

A signal processor generates a photoacoustic image based on a received signal, which is received at a plurality of positions by the acoustic wave detector. In order to process the electric signal acquired by the acoustic wave detector efficiently, it is preferable to have an A/D convertor that converts an analog signal into a digital signal. In terms of shortening the time required for generating an image, it is preferable that a plurality of received signals can be processed at the same time. According to this embodiment, the signal processor has a normalization processor and an imaging processor to be described below. The signal processor corresponds to the signal processor of the present invention in terms of performing the processing of received signals and the imaging processing.

(Normalization Processor)

A normalization processor normalizes a time series of received signal received at each position. The normalization processor converts the signal intensity so that the amplitude of the wave is 1 while maintaining the form of the wave (phase information of the frequency component) of the received signal. This processing is called "normalization processing". There are some methods for the normalization processing which will be described later. The normalization processor corresponds to the normalizer of the present invention.

(Imaging Processor)

The imaging processor generates a photoacoustic image inside the object from a time series of received signal received at each position, or a normalized signal generated by normalizing the received signal. A Delay and Sum algorithm, for example, can be used to form a photoacoustic image.

(Holding Unit)

A holding unit is used for holding an object, and is constituted by two holding plates, for example. This can prevent the object from moving and changing the position during measurement. Furthermore, pressure by the holding plate can make the object thinner, which allows imaging a deep portion of the object. For the holding plate located between the object and the acoustic wave detector, it is preferable that the absorption of light is low, the absorption of the acoustic wave is low, and the acoustic impedance difference from the object is small, and using polymethylpentene resin, for example, is desirable.

The above is a configuration of the photoacoustic measurement apparatus according to the present invention.

<Normalization Processing>

An overview and the effect of the processing performed by the normalization processor will be described using an example.

(Overview of Normalization Processing)

A case when a received signal is an analog signal will be described as an example.

First the received signal is Hilbert-transformed. By this transform, all the positive frequency components are advanced to 90°, and all the negative frequency components are delayed by 90°. The Hilbert transform signal g(t) is given by Expression (1) with respect to the original time series signal f(t) (t is time).

[Math. 1]

$$g(t) = \frac{1}{\pi} \int_{-\infty}^{\infty} \frac{f(\tau)}{t - \tau} d\tau \qquad (1)$$

Here a complex signal h(t) is determined by Expression (2).

$$h(t) = f(t) + ig(t) \qquad (2)$$

In this case, the absolute value of h(t) becomes an envelope signal of f(t). Here i denotes an imaginary unit.

If the original signal f(t) is divided by the envelope signal |h(t)|, a normalized signal, where the amplitude has been converted to 1, can be acquired. In other words, the normalized signal f_normal (t) is given by Expression (3).

[Math. 2]

$$f\_normal(t) = \frac{f(t)}{|h(t)|} = \frac{f(t)}{|f(t) + ig(t)|} \qquad (3)$$

This is the same for the case when the received signal is a digital signal. First the received signal f(n) (n denotes a sampled signal string number, corresponding to time) is discrete Hilbert-transformed. In concrete terms, discrete Fourier transform is performed on f(n), a value corresponding to the positive frequency by −i, and a value corresponding to the negative frequency by i, and then inverse Fourier transform is performed. Thereby a Hilbert transform signal g(n) is acquired. Here a complex number h(n) is determined by Expression (4).

$$h(n) = f(n) + ig(n) \qquad (4)$$

In this case, the absolute value of h(n) becomes an envelope signal of f(n). If the original signal f(n) is divided by the envelope signal |h(n)|, a normalized signal, where the amplitude has been converted to 1, can be acquired.

The normalized signal f_normal (n) is given by Expression (5).

[Math. 3]

$$f\_normal(n) = \frac{f(n)}{|h(n)|} = \frac{f(n)}{|f(n) + ig(n)|} \quad (5)$$

Another possible method for normalization processing is that a received signal is divided into a plurality of blocks sectioned each time the positive and negative invert, the signal is linearly transformed so that the amplitude becomes 1 or −1 in each block, then the transformed signal is integrated into one time series signal, whereby a normalized signal is acquired.

(Effect of Normalization Processing)

The reason why the normalization processing decreases artifacts that are generated due to an interfacial photoacoustic wave and a multi-reflected photoacoustic wave will be described.

After the normalization processing is performed, the normalized signal no longer has the signal intensity information, but still has information on the form of the waveform, that is the phase information for each frequency, at a certain time.

Normally an image generation algorithm, such as Delay and Sum, is based on the assumption that an acoustic wave diverges from a point acoustic wave source as a spherical wave, and reaches the acoustic wave detector. Then a time series signal of the acoustic wave detector, located at a receivable position, is added (phasing addition), considering time delay due to acoustic wave propagation, so as to calculate the photoacoustic image intensity at a certain voxel. Here a voxel is a unit area assuming that three-dimensional image reconstruction is performed, and a pixel is a unit area if two-dimensional image reconstruction is performed.

Now a case of performing image formation assuming that a point acoustic wave source, a line acoustic wave source or a surface acoustic wave source exists in a voxel is considered.

An acoustic wave from a line acoustic wave source diverges as a cylindrical wave and reaches the acoustic wave detector, so the degree of correlation when phasing addition is performed is smaller than the case of a point acoustic wave source. An acoustic wave from a surface acoustic wave source diverges as a plane wave and reaches the acoustic wave detector, so the degree of correlation when phasing addition is performed is even smaller. The amplitude of a normalized signal after the normalization processing is performed is 1, therefore the magnitude relationship of the image intensity when the photoacoustic image is formed, based on the normalized signal, is as shown in Expression (6).

$$F1 > F2 > F3 \quad (6)$$

Here F1 denotes an image intensity of the point acoustic wave source, F2 denotes an image intensity of the line acoustic wave source, and F3 denotes an image intensity of the surface acoustic wave source.

An interfacial photoacoustic wave or a multi-reflected photoacoustic wave are regarded as a wave from a surface acoustic wave source, so artifacts, generated due to the interfacial photoacoustic wave or the multi-reflected photoacoustic wave, can be decreased more compared with the image intensity of the photoacoustic images generated by a point acoustic wave source or a line acoustic wave source.

A more detailed configuration will be described in the following examples.

Example 1

FIG. 1 is a conceptual diagram depicting an example of a photoacoustic measurement apparatus of the present invention. In FIG. 1, the reference numeral 101 denotes a pulsed light source constituted by a titanium sapphire laser that generates pulsed light of which wave length is 800 nm, pulse width is 20 nsec, repetition frequency is 10 Hz, and pulse energy is 30 mJ. The reference numeral 103 denotes an optical transmission unit constituted by a bundle fiber, and the reference numeral 105 is an optical irradiation unit.

The reference numeral 107 denotes an object, and the reference numerals 109 and 111 denote holding plates between which the object is held. The holding plates 109 and 111 are made from polymethylpentene resin, of which thickness is 10 mm.

The reference numeral 113 denotes an acoustic wave detector in which elements are arranged in a two-dimensional array. The reference numeral 106 denotes irradiated light, which is emitted by the optical irradiation unit 105. An angle of the irradiated light is adjusted by an optical system (not illustrated), such as a prism, installed inside the optical irradiation unit 105, so that the irradiated light 106 contacts the object 107 in front of the acoustic wave detector 113. Water (not illustrated) is filled between the acoustic wave detector 113 and the holding plate 109 to easily propagate the acoustic wave.

In the acoustic wave detector 113 used in this example, a piezoelectric element (transducer) of which element size is 2 mm square, element pitch is 2 mm, and central detection frequency is 1 MHz is two-dimensionally arrayed as 8 elements horizontally and 23 elements vertically.

A time series of received signal, received by the acoustic wave detector 113, is converted into a digital signal by an A/D convertor 115 (ADC), and is then converted into a normalized signal by being normalized by a normalization processor 117 so that the amplitude becomes 1. A first image signal 120 (which corresponds to the first image data), formed by an imaging processor 119 based on the normalized signal, is displayed by an image display unit 121.

FIG. 2 is a set of diagrams depicting the object to be measured in this example. FIG. 2A shows a phantom, that is the object viewed from the z direction, and FIG. 2B is the phantom viewed from the x direction. The result of measuring this object by the photoacoustic measurement apparatus will now be described.

In FIG. 2, the reference numeral 151 denotes the phantom (simulated biological object) of which absorption coefficient and scattering coefficient are those of a human breast. The size of the phantom 151 is 120 mm wide, 60 mm high and 40 mm thick. The reference numerals 153, 155 and 157 denote wire-like light absorbers (about 2 mm in diameter) which are embedded in the phantom 151 at positions that are about 25 mm in the thickness direction at 10 mm intervals, and have been adjusted so that the absorption coefficient (ABS) is greater in the sequence of 153 to 157.

The acoustic wave detector is disposed in the hatched area (acoustic wave detector area 158) in FIG. 2A, and the size of this area 158 is 16 mm×46 mm. The pulsed light irradiation area is matched with the acoustic wave detector area 158 in advance. An imaging area 159 in FIG. 2B is an area considering the size of the acoustic wave detector, and will be described in detail later.

Figure 3A:
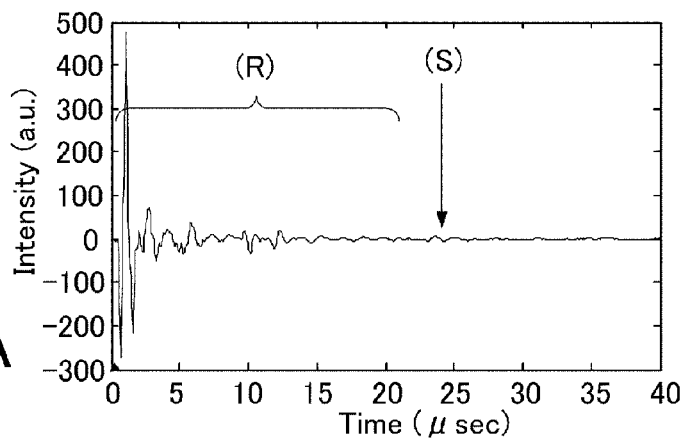
FIG. 3A to FIG. 3C are diagrams depicting a normalized signal of Example 1.

FIG. 3A shows an A/D converted received signal that is received by an element of the acoustic wave detector 113. In FIG. 3A, the abscissa is an elapsed time from 0 when the pulsed light was irradiated, and the ordinate is an intensity of the received acoustic wave. In FIG. 3A, the signal (S) which arrived after about 25 μsec has elapsed is the signal from the light absorber. The signal (R) which arrived during 20 μsec from the time 0 is an interfacial photoacoustic wave generated on the surface or on the interface between the phantom and the holding plate, or a multi-reflected photoacoustic wave reflected on the interface of the holding plate or the like.

Figure 3B:
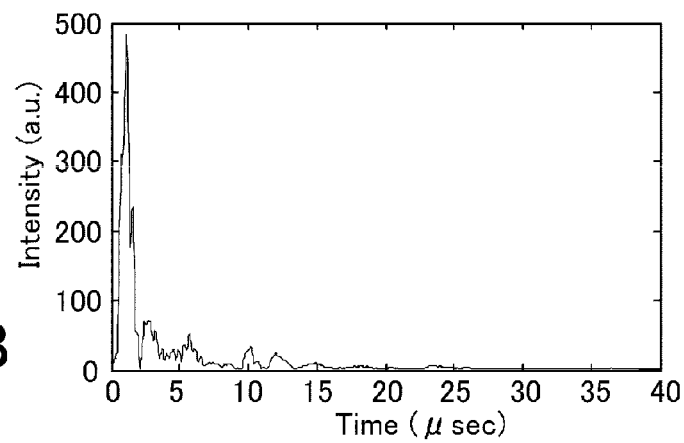
Figure 3C:
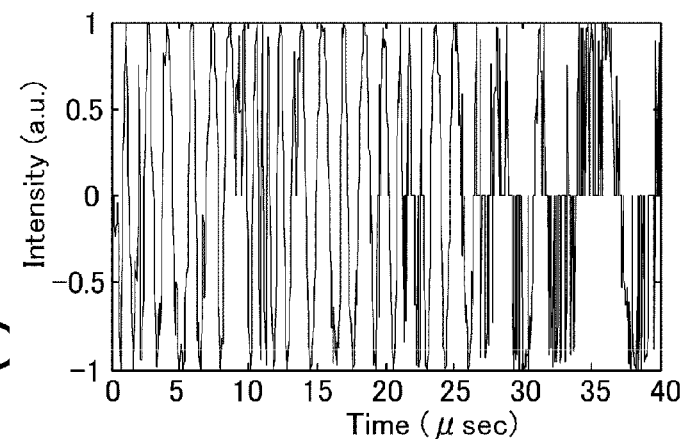

FIG. 3B shows an envelope signal of the signal shown in FIG. 3A. A normalized signal is acquired by dividing the signal in FIG. 3A by the envelope signal. FIG. 3C shows the normalized signal. As FIG. 3C shows, the amplitude of the signal is normalized to 1, and the form of the wave is maintained.

Figure 4A:
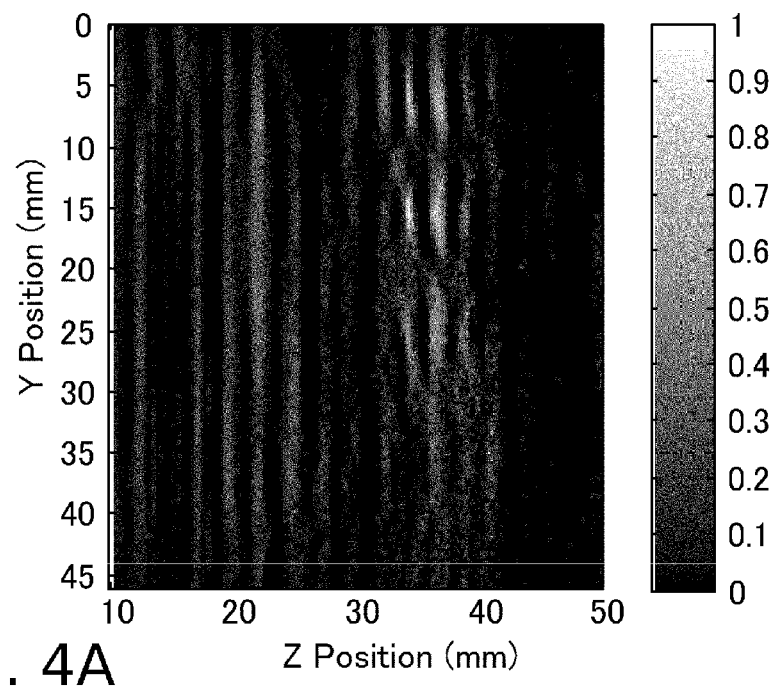
FIG. 4A and FIG. 4B are diagrams depicting an image signal of Example 1.

FIG. 4A shows an example when a normalized signal is generated from the received signal received by all the elements of the acoustic wave detector 113, and an image signal (first image signal) is generated from the normalized signal. In this case, considering the directional angles of the elements, elements to which an acoustic wave from a voxel enters at an angle of ±25° are used for image formation. The maximum value of the image signal in each voxel is normalized to 1, and is rounded up to 0 if the image signal of each voxel is a negative value.

Figure 4B:
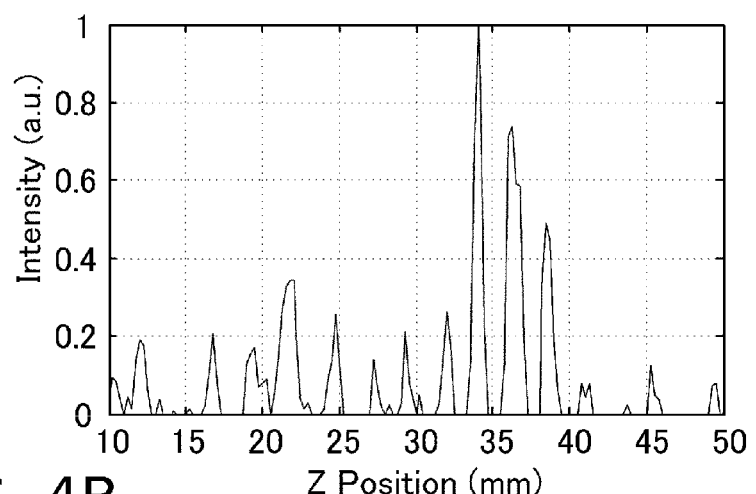

FIG. 4A shows a yz plane (cross-section) when a phantom is sectioned at the center of the acoustic wave detector in the x direction. Considering the thickness 10 mm of the holding plate, 10 mm to 50 mm are indicated in the z direction (abscissa). Further, considering the size of the acoustic wave detector, 0 mm to 46 mm are indicated in the y direction (ordinate) (corresponding to the image area 159 enclosed by a dotted line in FIG. 2B). FIG. 4B shows a waveform when the phantom is sectioned at 16 mm in the y direction in FIG. 4A.

Figure 5A:
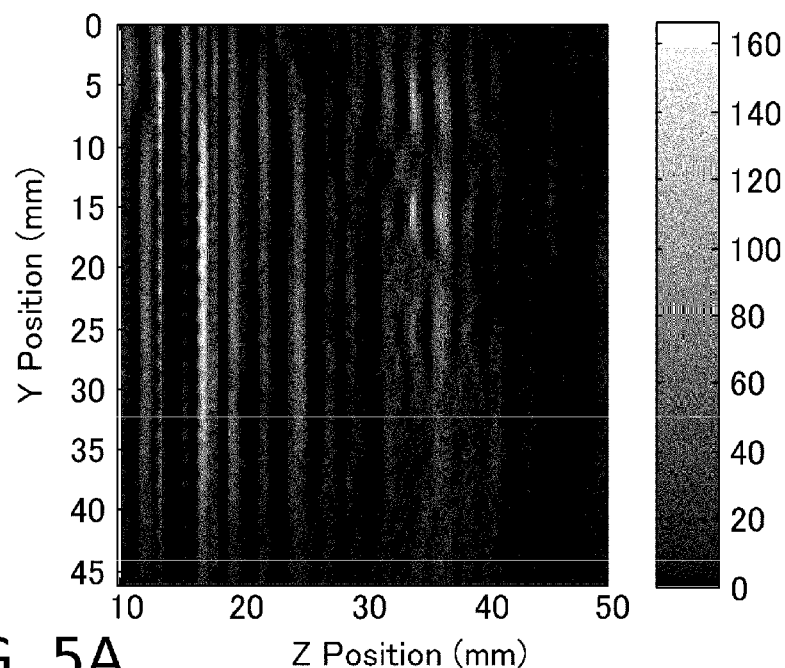
FIG. 5A and FIG. 5B are diagrams depicting a comparison example.
Figure 5B:
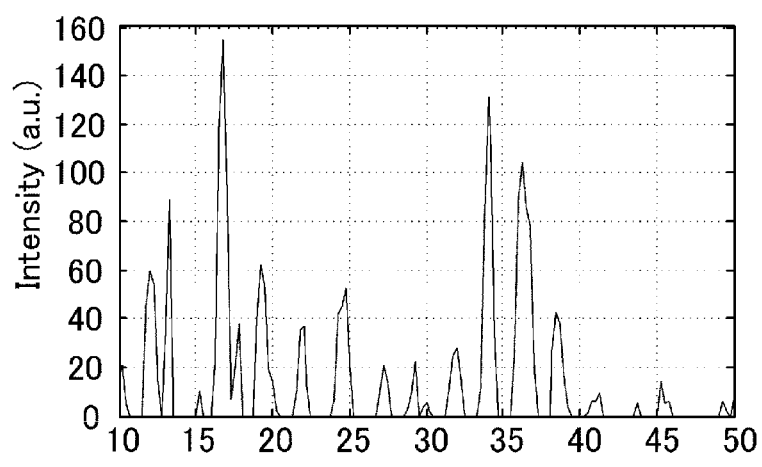

FIG. 5A and FIG. 5B show a comparison example of generating an image signal from a non-normalized received signal. The indicated coordinates are the same as FIG. 4.

In FIG. 5, the size of the image of the light absorber that appears at around 35 mm in the z position is smaller than or similar to the image generated by the interfacial photoacoustic wave or multi-reflected photoacoustic wave (artifact) that appears at 10 mm to 30 mm in the z direction. As FIG. 4 shows, according to this example, the image generated by the interfacial photo acoustic wave or multi-reflected photoacoustic wave (artifact) is suppressed, and the contrast of the image of the light absorber is improved. This demonstrates the effect of this example.

The image that appeared at 16 mm in the y direction corresponds to the light absorber 155, and the image that appears at 6 mm in the y direction corresponds to the light absorber 157. This sequence does not match with the magnitude relationship of the absorption coefficients. This is because irradiation of the light is weaker in the peripheral area compared with the center area, and the light absorber 157 exists at an edge of the imaging area and the number of elements used for forming the image is few, which is not an essential problem for the present invention.

The image of the light absorber is doubled in the z direction at several mm apart, but this is due to multi-reflection inside an acoustic impedance matching layer disposed in the detection unit of the acoustic wave detector, which is not an essential problem for the present invention.

In this example, the optical irradiation unit and the acoustic wave detector may be integrated, and scan the measurement area two-dimensionally in order to widen the measurable area. This is effective to measure an object that is larger than the size of the acoustic wave detector. Further, in order to enhance the irradiation light, another optical irradiation unit may be installed in such a way that light can be irradiated onto the object from the holding plate on the opposite side (which corresponds to reference numeral 111 in FIG. 1) of the ultrasonic detector.

Example 2

Figure 6:
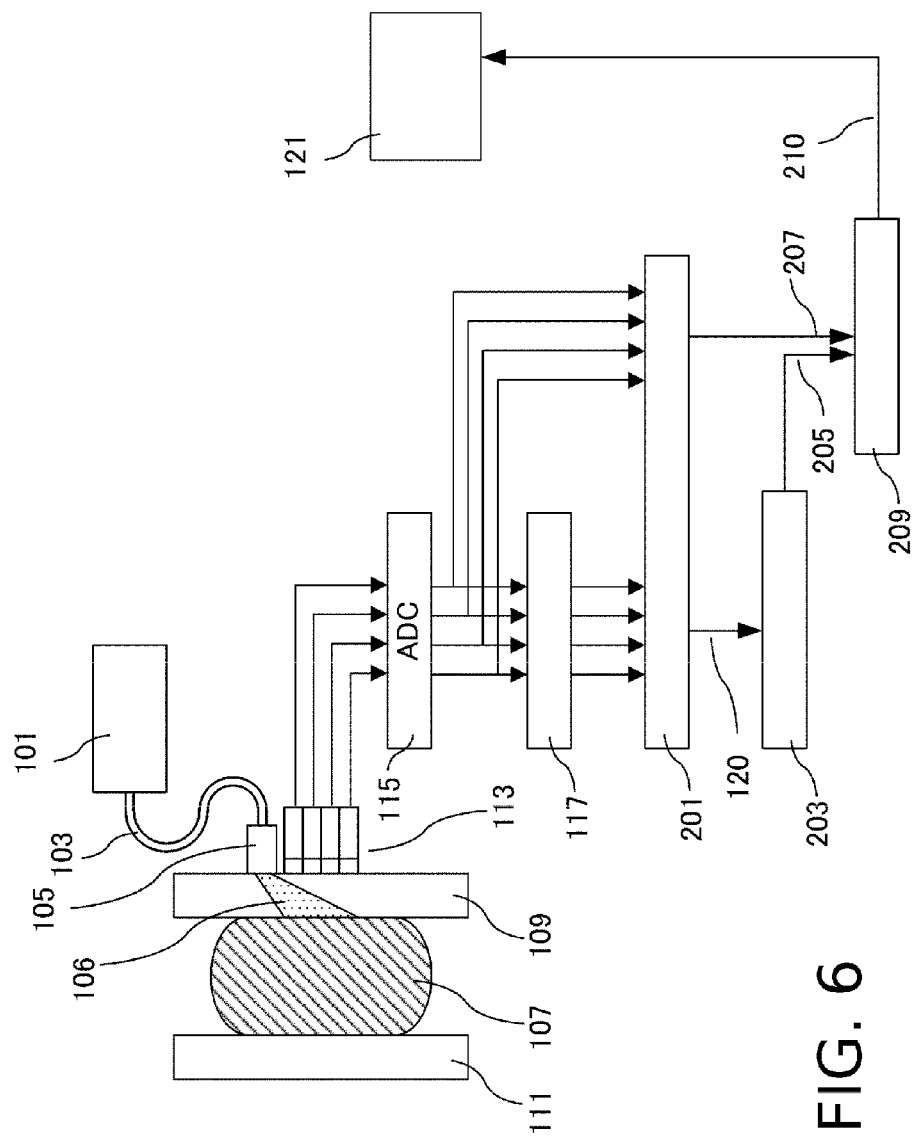
FIG. 6 is a conceptual diagram depicting a configuration of an apparatus of Example 2.

FIG. 6 is a conceptual diagram depicting Example 2 of the photoacoustic measurement apparatus of the present invention. A composing element the same as FIG. 1 is denoted with a same reference numeral, for which description is omitted.

An imaging processing unit 201 generates a first image signal 120 from a received signal normalized in the same method as Example 1, and generates a second image signal 207 (which corresponds to the second image data) from the non-normalized received signal. The first image signal 120 is converted into a correction map 205, where a correction value for each voxel is mapped, by a correction map generation unit 203.

Then in the image correction unit 209, each voxel data of the second image signal 207 is multiplied by the voxel data of the correction map 205 in each corresponding position. Thereby a final image signal 210 (which corresponds to the third image data) is acquired. In other words, the correction map is generated by determining, for each unit area inside the object, a coefficient to be used for correction to acquire a final image signal.

Figure 7:
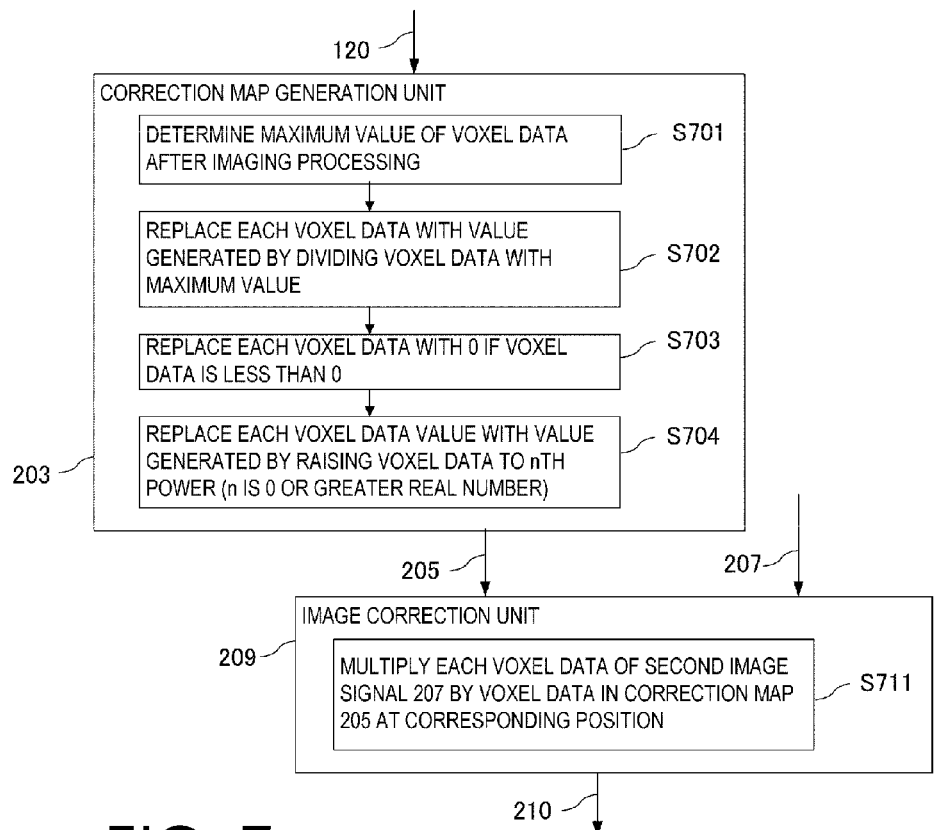
FIG. 7 is a flow chart depicting a correction map according to Example 2.

Processing by the correction map generation unit 203 and the image correction unit 209 will be described with reference to the flow chart in FIG. 7.

In step S701, the correction map generation unit 203 determines a maximum value in all the voxel data after the imaging processing.

In step S702, each voxel data of the first image signal 120 is divided by the maximum value determined in S701. Then each voxel data is replaced with a value generated by dividing the voxel data by the maximum value.

In step S703, voxel data of which value after replacement is less than 0 is replaced with 0.

In step S704, each voxel data is replaced with a value generated by raising the value of each voxel data to the nth power (n is 0 or greater real number). The voxel data generated by this processing is a correction map 205. The value n can be set to a relatively large value if the peak value is emphasized, and to a relatively small value if weak image signals are maintained.

In step S711, the image correction unit 209 multiplies each voxel data of the second image signal 207 by the voxel data of the correction map 205 of a corresponding position. Thereby a final image signal 210, to be provided to the image display unit, is generated.

A result of measuring the object shown in FIG. 2 by the photoacoustic measurement apparatus of this example will now be described.

The image shown in FIG. 4 is an example when the first image signal 120 is extracted at a certain plane, and the image in FIG. 5 is an example of the second image signal 207. FIG. 4 is a result when the values are already converted, so that the maximum value is 1 and the minimum value is 0. If n is 1, the correction map 205 is the same as FIG. 4. In other words, in this plane, the image data in FIG. 5 is multiplied by the image data in FIG. 4. FIG. 8 shows the result.

Figure 8A:
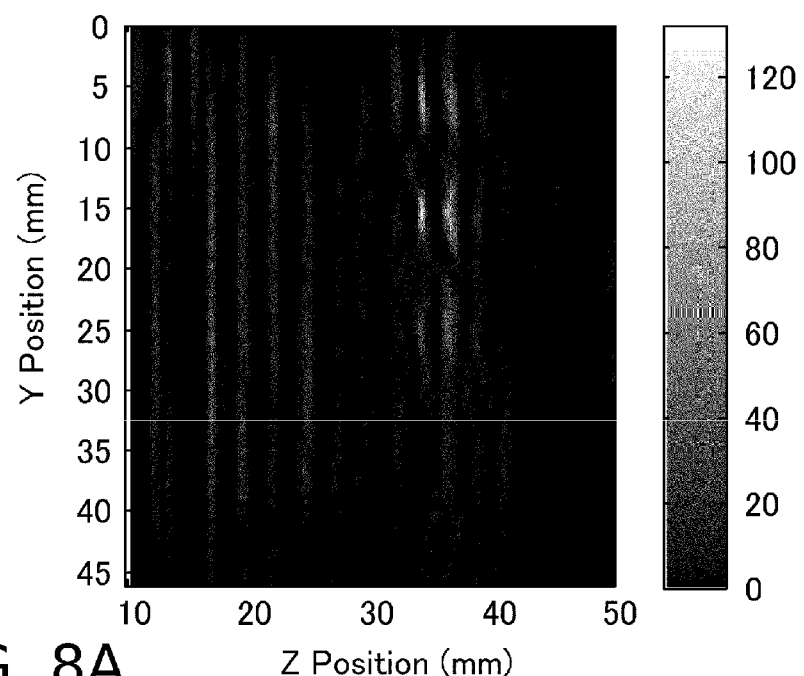
FIG. 8A and FIG. 8B are diagrams depicting an image signal of Example 2.
Figure 8B:
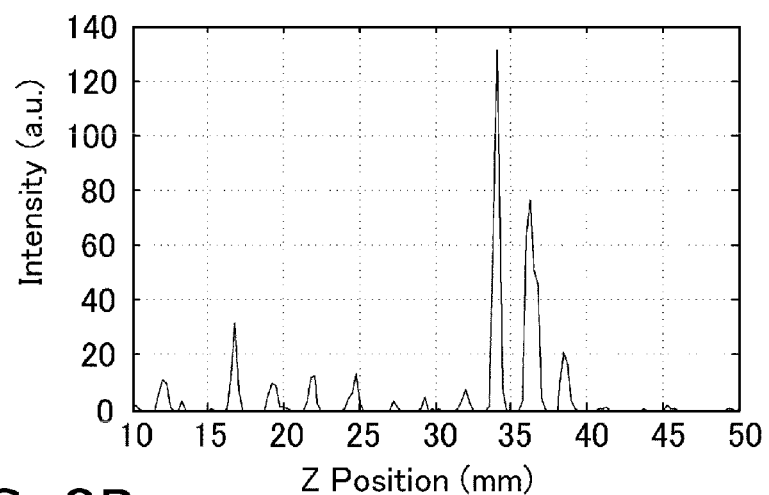

FIG. 8A shows a yz plane (cross-section) when a phantom is sectioned at the center of the acoustic wave detector in the x direction. FIG. 8B shows a waveform when the phantom is sectioned at 16 mm in the y direction in FIG. 8A.

In FIG. 8, just like Example 1, an image generated by the interfacial photoacoustic wave or multi-reflected photoacoustic wave (artifact) is suppressed, and the contrast of the image of the light absorber is improved. Furthermore, the intensity of the image of the light absorber is almost the same as FIG. 5. This means that the intensity value of the image signal generated from the non-normalized received signal is maintained. Therefore according to this example, a higher contrast of the image can be implemented without losing a desired target intensity information.

In this example, the coefficient n can be set according to the image, based on the desired target intensity information and the intensity information of the artifact, and the apparatus may be configured such that the operator can input and set the configuration during operation.

Example 3

Example 3 has a configuration which allows imaging without losing intensity information, just like Example 2. The difference from Example 2 is the correction map generation method, and the rest is the same as the configuration in FIG. 6.

Figure 9:
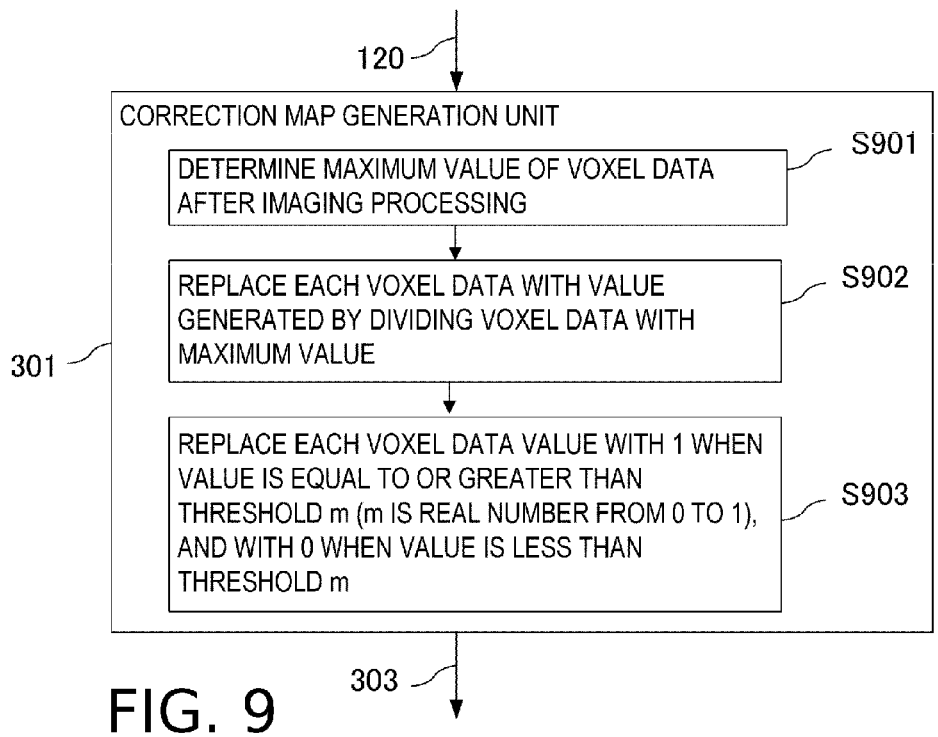
FIG. 9 is a flow chart depicting a correction map according to Example 3.

Processing by the correction map generation unit 301 according to this example will be described with reference to the flow chart in FIG. 9.

In step S901, a correction map generation unit 301 determines a maximum value in all the voxel data after the imaging processing.

In step S902, each voxel data of the first image signal 120 is divided by the maximum value determined in S901. Then each voxel data is replaced with a value generated by dividing the voxel data by the maximum value.

In step S903, when a predetermined threshold is represented by m, voxel data of which value after the replacement is the threshold or more (m or more) is replaced with 1, and voxel data of which value after the replacement is less than the threshold (less than m) is replaced with 0. Here m is a real number from 0 to 1.

The voxel data generated by this processing is a correction map 303.

Just like Example 1, a result of measuring the object shown in FIG. 2 by the photoacoustic measurement apparatus according to this example will now be described.

Figure 10:
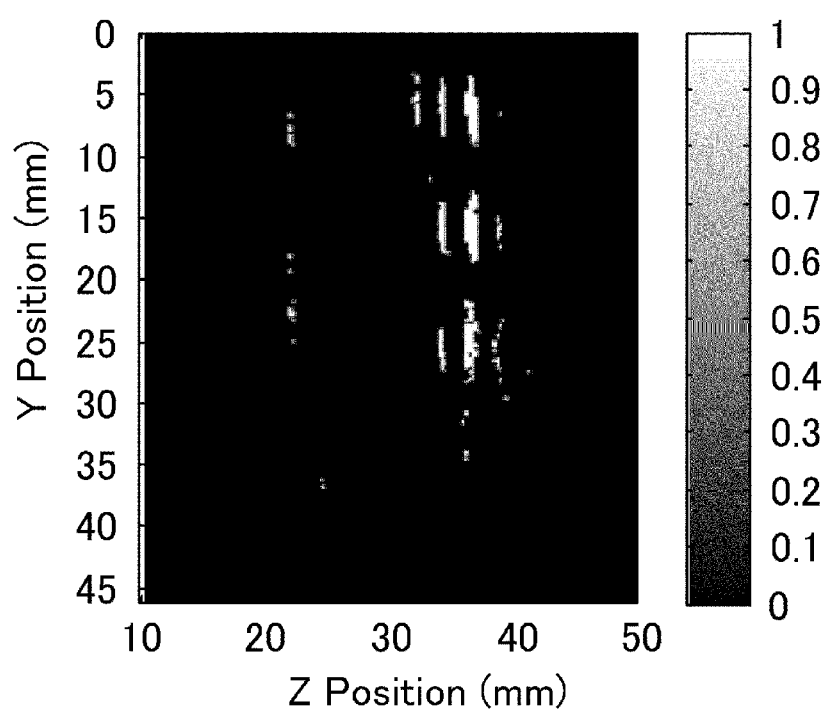
FIG. 10 is a diagram depicting the correction map according to Example 3.

The image shown in FIG. 4 is an example when the first image signal 120 is extracted at a certain plane. FIG. 4 is a result when the values are already converted, so that the maximum value is 1 and the minimum value is 0. FIG. 10 shows an example when the correction map 303, of which m is 0.4, is extracted at the same plane. FIG. 11 shows a result when the image data in FIG. 10 is multiplied by the image data in FIG. 4.

Figure 11A:
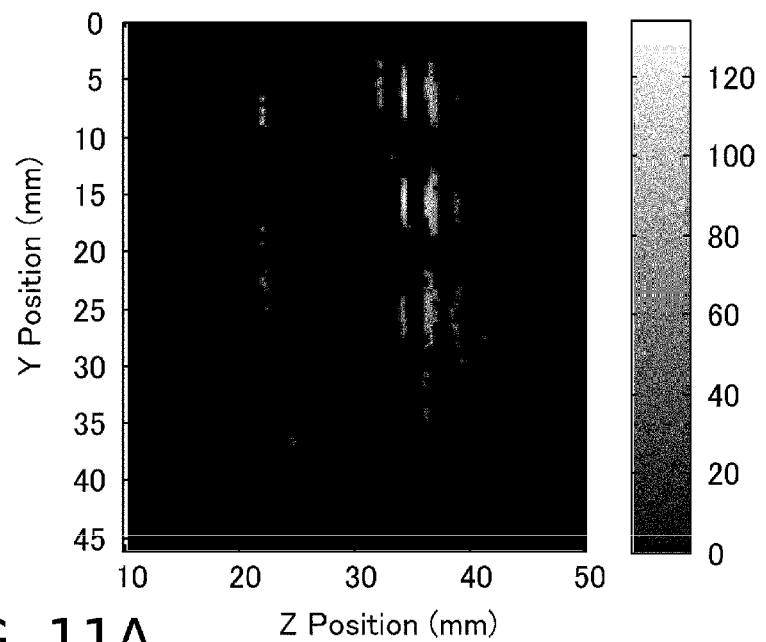
FIG. 11A and FIG. 11B are diagrams depicting an image signal of Example 3.
Figure 11B:
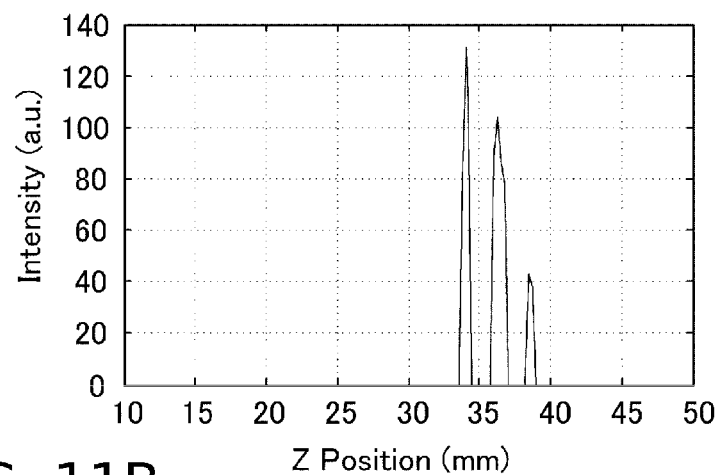

FIG. 11A shows a yz plane (cross-section) when a phantom is sectioned at the center of the acoustic wave detector in the x direction. FIG. 11B shows a waveform when the phantom is sectioned at 16 mm in the y direction in FIG. 11A.

In FIG. 11, the intensity of the image of the light absorber matches with FIG. 5, and the intensity value of the image signal is maintained. Further, the image generated by the interfacial photoacoustic wave or multi-reflected photoacoustic wave (artifact) is sufficiently suppressed. Therefore according to this example, a higher contrast of the image can be implemented without losing a desired target intensity information.

In this example, the threshold m can be set according to the image, based on the desired target intensity information and the intensity information of the artifact, and the apparatus may be configured such that the operator can input and set the threshold m during operation.

The method for generating the correction map from the image signal generated from the normalized received signal is not limited to the method disclosed in Example 2 and Example 3. An appropriate correction function matching the image may be used.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-128980, filed on Jun. 6, 2012, which is hereby incorporated by reference herein in its entirety.

What is claimed is:

1. An object information acquiring apparatus, comprising:
    a receiver configured to convert an acoustic wave generated from an object irradiated with light into a received signal and output the received signal in a time series;
    a normalizer configured to generate a Hilbert-transform signal by performing Hilbert-transform on the received signal and generate a normalized signal by calculating a ratio between an intensity of the received signal and an absolute value of a complex signal which represents the received signal as real part and the Hilbert-transform signal as imaginary part; and
    a processor configured to generate, based on the normalized signal, first image data.

2. The object information acquiring apparatus according to claim 1, wherein said normalizer is configured to generate the normalized signal by dividing the intensity of the received signal by the absolute value of the complex signal.

3. The object information acquiring apparatus according to claim 1, wherein said processor is configured to generate the first image data by applying an image generation algorithm to the normalized signal.

4. The object information acquiring apparatus according to claim 1, wherein said processor is configured to:
    generate, based on the received signal, second image data that indicates a distribution of property information inside the object by applying an image generation algorithm to the received signal;
    generate a coefficient for correcting image data based on the first image data; and
    generate third image data by correcting the second image data by means of the coefficient.

5. The object information acquiring apparatus according to claim 4, wherein said processor is configured to determine a maximum value of the first image data by comparing a value in each unit area of a region represented by the first image data and to generates the coefficient by dividing the value in each unit area of the first image data by the maximum value.

6. The object information acquiring apparatus according to claim 5, wherein said processor is configured to generate the coefficient by dividing the value in the each unit area of the first image data by the maximum value and then raising a result of the division to the nth power (n being is a real number equal to 0 or greater).

7. The object information acquiring apparatus according to claim 4, wherein said processor is configured to generate the coefficient in a unit area of a region represented by the first image data as 1 when a value in the unit area of the first image data is a predetermined threshold or more, and to generate the coefficient in the unit area of the first image data as 0 when the value in the unit area of the first image data is less than the predetermined threshold.

8. The object information acquiring apparatus according to claim 4, wherein said processor is configured to generate the third image data by multiplying the second image data by the coefficient.

9. The object information acquiring apparatus according to claim 1, further comprising an A/D convertor configured to convert the received signal as an analog signal into a digital signal,
wherein said normalizer is configured to generate a frequency signal by performing discrete Fourier transform on the digital signal, to generate a corrected frequency signal by multiplying a value corresponding to the positive frequency of the frequency signal by −i and multiplying a value corresponding to the negative frequency of the frequency signal by i, and to generate the Hilbert-transform signal by performing inverse Fourier transform on the corrected frequency signal.

10. The object information acquiring apparatus according to claim 1, wherein said receiver includes a plurality of receiver elements.

11. The object information acquiring apparatus according to claim 1, further comprising a parallel plate configured to hold the object,
wherein said receiver includes a plurality of receiver elements arranged on said parallel plate.

12. An object information acquiring method, comprising the steps of:
generating a Hilbert-transform signal by performing Hilbert-transform on a received signal in a time series obtained by receiving an acoustic wave generated from an object irradiated with light;
generating a normalized signal by calculating a ratio between an intensity of the received signal and an absolute value of a complex signal which represents the received signal as real part and the Hilbert-transform signal as imaginary part; and
generating, based on the normalized signal, first image data.

13. An object information acquiring apparatus, comprising:
a receiver configured to convert an acoustic wave generated from an object irradiated with light into a received signal and output the received signal in a time series;
a normalizer configured to generate an envelope signal of the received signal and generate a normalized signal by calculating a ratio between the received signal and the envelope signal; and
a processor configured to generate, based on the normalized signal, first image data.

14. The object information acquiring apparatus according to claim 13, wherein said processor is configured to:
generate, based on the received signal, second image data; and
generate third image data by correcting the second image data using the first image data.

15. The object information acquiring apparatus according to claim 13, wherein said processor is configured to cause a display unit to display the first image data.

16. The object information acquiring apparatus according to claim 13, further comprising an A/D convertor configured to convert the received signal as an analog signal into a digital signal,
wherein said receiver includes a plurality of receiver elements, and
wherein said processor is configured to generate the first image data by applying an image generation algorithm to the normalized signal as the digital signal.

17. The object information acquiring apparatus according to claim 13, further comprising a paraellel plate configured to hold the object and an A/D convertor configured to convert the received signal as an analog signal into a digital signal,
wherein said receiver includes a plurality of receiver elements arranged on said parallel plate, and wherein said processor is configured to generate the first image data by applying an image generation algorithm to the normalized signal as the digital signal.

18. An object information acquiring method, comprising:
generating an envelope signal of a received signal obtained by receiving an acoustic wave generated from an object irradiated with light;
generating a normalized signal by calculating a ratio between the received signal and the envelope signal; and
generating, based on the normalized signal, first image data.

* * * * *